United States Patent
Gustafson et al.

(10) Patent No.: US 8,158,847 B2
(45) Date of Patent: Apr. 17, 2012

(54) WATER-VAPOUR IMPERMEABLE CARRIER MEMBER FOR USE IN AN ABSORBENT ARTICLE

(75) Inventors: Ingrid Gustafson, Åsa (SE); Ulrika Husmark, Mölnlycke (SE); Jenny Hildeberg, Landvetter (SE)

(73) Assignee: SCA Hygiene Products AB, Göteborg (SE)

( * ) Notice: Subject to any disclaimer, the term of this patent is extended or adjusted under 35 U.S.C. 154(b) by 527 days.

(21) Appl. No.: 12/086,918

(22) PCT Filed: Dec. 22, 2005

(86) PCT No.: PCT/SE2005/002027
§ 371 (c)(1),
(2), (4) Date: Jun. 20, 2008

(87) PCT Pub. No.: WO2007/073263
PCT Pub. Date: Jun. 28, 2007

(65) Prior Publication Data
US 2009/0005749 A1    Jan. 1, 2009

(51) Int. Cl.
*A61F 13/15* (2006.01)
(52) U.S. Cl. .................. 604/360; 604/359; 604/367
(58) Field of Classification Search .................. 604/359, 604/360, 367
See application file for complete search history.

(56) References Cited

U.S. PATENT DOCUMENTS

| | | | |
|---|---|---|---|
| 2,066,946 A | 1/1937 | Reiman | |
| 2,629,378 A | 2/1953 | Barton | |
| 3,490,454 A | 1/1970 | Goldfarb et al. | |
| 3,783,869 A | 1/1974 | Schnipper | |
| 4,518,696 A | 5/1985 | Gehrman et al. | |
| 6,649,806 B1 * | 11/2003 | Forsgren-Brusk et al. | ... 604/360 |
| 6,761,885 B1 | 7/2004 | Hakansson et al. | |
| 6,854,600 B1 | 2/2005 | Persson et al. | |
| 2003/0012810 A1 | 1/2003 | Cintio et al. | |
| 2004/0127866 A1 * | 7/2004 | Odorzynski | ................... 604/359 |
| 2004/0172001 A1 | 9/2004 | Tengberg et al. | |
| 2004/0243076 A1 | 12/2004 | Husmark et al. | |
| 2005/0165372 A1 * | 7/2005 | Bechert et al. | ................ 604/367 |

(Continued)

FOREIGN PATENT DOCUMENTS

EP    1 210 277 B1    6/2002

(Continued)

OTHER PUBLICATIONS

An English Translation of the Office Action (Notice of Reasons for Rejection) dated Jan. 4, 2011, issued in the corresponding Japanese Patent Application No. 2008-547149.

(Continued)

*Primary Examiner* — Jacqueline F. Stephens
(74) *Attorney, Agent, or Firm* — Buchanan Ingersoll & Rooney PC

(57) ABSTRACT

An absorbent article such as a sanitary napkin, panty liner, incontinence protector, diaper, includes an absorbent structure (4) with a first and a second side, a moisture sensitive additive (8), such as a bacterial composition, and a carrier member (10). The carrier member (10) includes a first and a second water-vapor impermeable material layer (12, 13), the material layers are sealed together by a sealing (11) to form a water-vapor impermeable volume (9) there between holding the moisture sensitive additive (8). The carrier member (10) is located on the first or the second side of the absorbent structure (4).

39 Claims, 4 Drawing Sheets

U.S. PATENT DOCUMENTS

2009/0227930 A1 * 9/2009 Crisp .............................. 602/48

FOREIGN PATENT DOCUMENTS

| | | |
|---|---|---|
| JP | 11-056903 | 3/1999 |
| JP | 2003-502225 T | 1/2003 |
| JP | 2003-520105 T | 7/2003 |
| RU | 2 224 017 | 2/2004 |
| WO | WO 84/04675 | 12/1984 |
| WO | WO 92/13577 A1 | 8/1992 |
| WO | WO 97/02846 A1 | 1/1997 |
| WO | WO 99/17813 A1 | 4/1999 |
| WO | WO 99/45099 A1 | 9/1999 |
| WO | WO 00/35502 A1 | 6/2000 |
| WO | WO 00/76878 | 12/2000 |
| WO | WO 01/52912 | 7/2001 |
| WO | WO 02/28446 A1 | 4/2002 |
| WO | WO 2004/101008 | 11/2004 |
| WO | WO 2004/105822 | 12/2004 |
| WO | WO2007/073246 | 6/2007 |

OTHER PUBLICATIONS

G.B. Hill et al., "Bacteriology of the Vagina", Duke University Medical Center Department of Obstetrics and Gynecology and Department of Medicine, pp. 23-29, 1984;86:23-39.
PCT/ISA/210, Jul. 18, 2006.
PCT/ISA/237, Jul. 18, 2006.
PCT/IPEA/409, Mar. 17, 2008.

* cited by examiner

US 8,158,847 B2

WATER-VAPOUR IMPERMEABLE CARRIER MEMBER FOR USE IN AN ABSORBENT ARTICLE

TECHNICAL FIELD

The present invention relates to an absorbent article, such as sanitary napkins, panty liners, incontinence protectors and diapers that comprises a carrier member holding a moisture sensitive additive such as a bacterial composition.

BACKGROUND OF THE INVENTION

The urogenital area harbors a complex microbial ecosystem comprising more than 50 different bacterial species (Hill et al., Scand. J. Urol. Nephrol. 1984; 86 (suppl.) 23-29). The dominating species in this area for fertile women are lactic acid producing bacteria belonging to the genus *Lactobacillus*. These lactic acid producing members are important for retaining a healthy microbial flora in these areas, and act as probiotic bacteria with an antagonistic effect against pathogenic microbial species. Lactic acid producing bacteria inhibit growth and colonization by other microorganisms by occupying suitable niches for colonization, by forming biofilms and competing for available nutrients, thereby excluding colonization by harmful microorganisms. Also, the production of hydrogen peroxide, specific inhibiting substances, such as bacteriocines, and organic acids (including lactic acid and acetic acid) that lower the pH, inhibit colonization by other microorganisms.

The microbial ecosystem of a healthy individual can be disturbed by the use of antibiotics, during hormonal changes, such as during pregnancy or use of contraceptives with estrogen, during menstruation, after menopause, in people suffering from diabetes etc. Also, microorganisms may spread from the anus to the urogenital area, thereby causing infections. This results in a disturbance of the normal microbial flora and leaves the individual susceptible to microbial infections that cause vaginitis, urinary tract infections and ordinary skin infections. Microorganisms commonly associated with these kinds of infections belong to the genera ° E. scherichia, Enterococcus, Psedomonas, Proteus, Klebsiella, Streptococcus, Staphylococcus, Gardnerella and *Candida*. Women are at particular risk due to their shorter distance between the anus and the urogenital tract; especially at risk are young women, who not yet have a well developed microflora in the urogenital area and older women, who no longer have a protective flora.

One way to reduce the problems with the kinds of infections described above is to have a good personal hygiene. However, excessive use of cleaning agents not only decreases the amount of harmful microbes, but can harm the beneficial microbial flora, again render it susceptible for pathogenic species to colonize and cause infections.

Alternatively, administration of lactic acid producing bacteria to the urogenital area and the skin in order to outcompete pathogenic species and facilitate reestablishment and maintenance of a beneficial microbial flora in these areas, have been found to be a successful means to treat and prevent microbial infections.

It has been suggested that lactic acid producing bacteria can be delivered via absorbent products, such as diapers, sanitary napkin, incontinence guards, panty liners and tampons, as described in, for example, WO 92/13577, WO 97/02846, WO 99/17813, WO 99/45099 and WO 00/35502.

A major problem with providing products intended to be used for transfer of lactic acid producing bacteria, is that the bacteria have to retain viability during transport and storage of the products. Lactic acid producing bacteria rapidly loose viability under semi-moist conditions, and it is therefore important that the bacteria are not uncontrollably exposed to moisture. With "semi-moist" conditions is meant that the water activity (aw) is between about 0.2 and about 0.9. One way to partly overcome this problem in absorbent products provided with lactic acid producing bacteria has been to supply the products with the bacteria, drying said products to remove most of the moisture and enclosing the products in moisture impervious packages (WO 99/17813; EP B1 1 210 277). However, since the entire absorbent product is packed together with the moisture sensitive bacteria, it is necessary, as stated above to dry said absorbent product to a high extent.

This is in conventional processes for producing absorbent articles very difficult to achieve. This is also an inflexible solution since once the product has been dried it is necessary to enclose it quickly in the moisture impervious package before moisture starts to act on the lactic acid producing bacteria. Further since these moisture impervious packages are produced from expensive films these kinds of large packages are quite costly.

An alternative way to protect bacteria against moisture has been to disperse the bacteria in a hydrophobic substance (see e.g. U.S. Pat. No. 4,518,696; WO 92/13577; WO 02/28446) which due to its hydrophobic character will prevent moisture to reach the embedded bacterial cells. The problem with this is that when folding and packaging the product the hydrophobic substance wherein the bacteria is dispersed sticks to the package or smears over the product in an undesired manner which makes the product look messy. If the hydrophobic substance is smeared over the topsheet this may also have a negative impact on the absorbance due to clogging of the pores in the topsheet. The desired effect may also be reduced since some of the bacteria disappears with the package when removing the package or alternatively ends up on a location on the product where it does not come in direct contact with the urogenital area upon usage.

OBJECTS AND SUMMARY

Consequently, prior to the present invention there was still a need to develop improved ways of protecting moisture sensitive additive such as lactic acid producing bacteria so that it is ensured that these additives will not be harmed or destroyed and which will also ensure that the properties of the product are retained. In addition, there was still a need to develop manufacturing processes that are efficient and less expensive.

The above defined problems are solved by an absorbent article comprising an absorbent structure with a first and a second side, a moisture sensitive additive and a carrier member, wherein said carrier member comprises a first and a second water-vapour impermeable material layer, said material layers being sealed together by a sealing to form a water-vapour impermeable volume there between holding said moisture sensitive additive, said carrier member being located on the first or the second side of the absorbent structure.

Said water-vapour impermeable material layer and said sealing are as herein below explained designed to prevent diffusion of water-vapour into said volume holding said moisture sensitive additive.

In one aspect said first and/or second material layers comprise a metal foil. In a further aspect said metal foil is aluminium. In order to secure that said volume is water-vapour impermeable and at the same time balance this with the requirement of having a thin film for cost reasons, said metal foil has in a still further aspect, a thickness of at least 2 µm, preferably between 5-20 µm and most preferably between 7-10 µm.

According to one embodiment said first and/or second material layers comprise a metal oxide layer, for example an aluminium oxide layer, and/or a silicon oxide layer.

According to a further embodiment said first and/or second material comprises a polymeric film. Said polymeric film may be chosen from polyethylene, polypropylene, polyesters, polyvinyl chloride, polyvinyl dichloride, cyclic olefinic copolymers, copolymers and mixtures thereof, metallised polyolefins and plastic laminates with ceramic barrier. Such polymeric materials are known to have good water vapour barrier properties.

In one aspect said first and/or second material comprises a laminate comprising said polymeric film.

According to another aspect said first and second material layers comprise a laminate of a metal foil and a polymeric material and/or a wax. In a further aspect said laminate comprises at least three laminate layers.

Said polymeric material is chosen from polyethylene, polypropylene, polyesters, polyethylene terephthalate, polyvinylchloride, polyvinyldichloride, cyclic olefinic copolymers, polyolefins, metallized polyolefins, ethylene vinylacetate copolymers, ethylene ethyl acrylate copolymers, ethylene butyl acrylate copolymers, polyamides, polyvinyl alcohol, ionomers, copolymers and mixtures thereof and plastic laminates with ceramic barrier. Furthermore said wax is chosen from a plant wax, a mineral wax, an animal wax, a silicon wax and mixtures thereof.

In one aspect said polymeric material or said wax is forming the interior laminate layer facing the moisture sensitive additive.

In another aspect said polymeric material is forming the exterior laminate layer facing away from the moisture sensitive additive.

In a further aspect both said interior laminate layer and said exterior laminate layer is formed by a polymeric material and/or a wax.

The exterior laminate layers are chosen with the purpose of having a strong wear and tear resistance and at the same time be comfortable against the user's skin. The interior laminate layers are often chosen with the purpose of obtaining a good sealing.

According to one embodiment said polymeric material or wax forms said sealing around said water-vapour impermeable volume.

With the purpose of increasing the time it takes for the water-vapour to diffuse into the volume, according to one embodiment said sealing of said water-vapour impermeable volume has a width of at least 1 mm, preferably 3 mm and most preferably 5 mm.

In order to have a good transfer of the moisture sensitive additive to the users skin and at the same time ensure that the absorbent article has a good absorption, according to one aspect the length of said carrier member is 1-15 cm, preferably 2-8 cm, most preferably 2-5 cm. In a further aspect the width of said carrier member is 0.5-5 cm, preferably 0.8-3 cm, most preferably 1-2 cm.

In one embodiment in which the absorbent article comprises a liquid-permeable topsheet and a backsheet, wherein said absorbent structure is located between the topsheet and the backsheet, said carrier member is located on the wearer facing side of said topsheet. In another embodiment the carrier member is located between said topsheet and said absorbent structure.

In one aspect said carrier member is formed by placing two material layers on one another with the moisture sensitive additive there between and sealing the open edges formed between the two materials layers. The two separate material layers may be of the same or of two different materials.

In another aspect the carrier member is formed by folding one material layer into two material layers and seal with the moisture sensitive additive located between the folded material layers and sealing together the folded material layers along the open edges.

In one embodiment said moisture sensitive additive is a bacterial composition. In a further aspect the bacterial composition is in the form of a dry powder. In another aspect the bacterial composition is dispersed in or applied to a delivery vehicle or a support member. Said delivery vehicle may for example be a hydrophobic composition. Said support member for the bacterial composition may for example be a fibrous material or an adhesive, for example an adhesive film, onto which the bacterial composition is applied.

In one embodiment said bacterial composition contains lactic acid producing bacteria.

In a preferred embodiment said lactic acid producing bacteria is *Lactobacillus plantarum* 931.

The absorbent article may comprise at least two of said carrier member containing the moisture sensitive additive. Preferably they are spaced apart in the longitudinal direction of the article.

Before using the absorbent article one of the material layers of the carrier member should be removed or ruptured in order to expose the wearer for the bacterial composition or in order to expose the absorbent article to the odour-inhibiting composition. In one embodiment the carrier member is opened by a pull string having a free end and while the rest of the pull string is integrated into the carrier member. Upon pulling the pull string the material layer/layers will be peeled of or ruptured. In another embodiment the carrier member is opened by peeling of one of the material layers and in a further embodiment by rupturing one of the material layers.

DEFINITIONS

Figure 1:
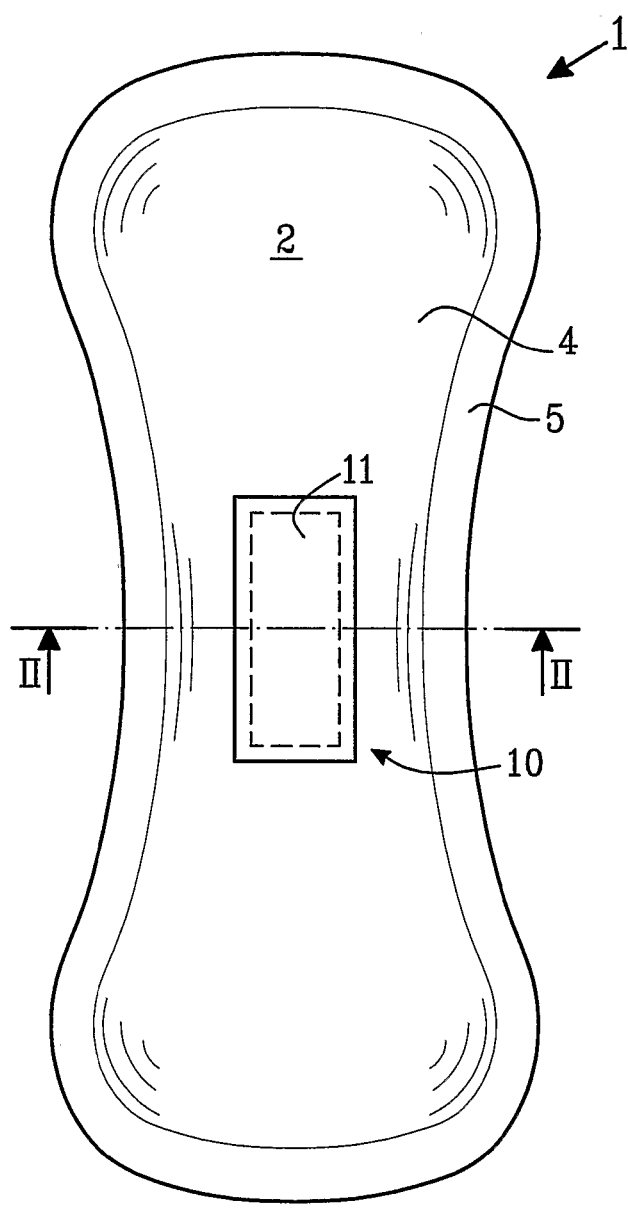
FIG. 1 is a plan view of an embodiment of an absorbent article according to the present invention.

The term "absorbent article" refers to products that are placed against the skin of the wearer to absorb and contain body exudates, like urine, faeces and menstrual fluid. The disclosure mainly refers to disposable absorbent articles, which means articles that are not intended to be laundered or otherwise restored or reused as an absorbent article after use. Examples of disposable absorbent articles include feminine hygiene products such as sanitary napkins, panty liners and sanitary panties; diapers and pant diapers for infants and incontinent adults; incontinence pads; diaper inserts and the like.

By "moisture-sensitive additives" is meant additives that are intended to contribute to the effect and function of the product in some way and whose properties may be impaired when they are exposed to uncontrolled levels of moisture, e.g. in storage. Examples of such moisture-sensitive additives are moisture sensitive bacterial compositions, such as lactobacilli, and odour-inhibiting additives, such as zeolites and silica.

By "probiotic composition" or "bacterial composition" is meant a composition comprising probiotic bacteria, i.e. bacteria that have the ability to reestablish the natural microbial flora of the host.

"Water activity" $a_w$ measures the vapour pressure generated by the moisture present in a hygroscopic product.

$a_w = p/p_s$, where:

p: partial pressure of water vapour at the surface of the product
$p_s$: saturation pressure, or the partial pressure of water vapour above pure water at the product temperature Water activity reflects the active part of moisture content or the part which, under normal circumstances, can be exchanged between the product and its environment.

Water activity is usually defined under static conditions of equilibrium. Under such conditions, the partial pressure of water vapour (p) at the surface of the product is equal to the partial pressure of water-vapour in the immediate environment of the product. Any exchange of moisture between the product and its environment is driven by a difference between these two partial pressures.

By "dispersion" is meant a mixture of at least two phases, which are insoluble or limitedly soluble in one another, wherein one phase forms solid particles, liquid droplets or gas bubbles in the other phase.

Preferred "lactic acid producing bacteria" includes bacteria from the genera *Lactobacillus, Lactococcus* and *Pediococcus*. Preferably the selected bacterium used is from the species *Lactococcus lactis, Lactobacillus acidophilus, Lactobacillus curvatus* or *Lactobacillus plantarum*. More preferably the bacterial strain is selected from *Lactobacillus plantarum*. Even more preferably the lactic acid producing bacterium is *Lactobacillus plantarum* 931 (deposition No. (DSMZ): 11918).

By a "water-vapour impermeable" material layer is meant a material layer whose impermeability is so high that a carrier member comprised of said material layer will not allow more moisture to enter than that at which uptake the active moisture-sensitive additive present in the carrier member will essentially retain their properties. This means that the carrier member may have a highest WVTR (Water Vapour Transmission Rate) of 6 g/m²/24 h according to ASTME 398-83 at 37.8° C. (100° F.) and 90% relative humidity, preferably at most 4 g/m²/24 h, and more preferably at most 2 g/m²/24 h, even more preferably at most 1 g/m²/24 h and even more preferably at most 0.1 g/m²/24 h. The material layer used will also preferably protect the moisture-sensitive additives in such a way that said additives will retain their effect for at least 6 months and preferably for 9 months in 23° C. (73.4° F.) and 50% relative humidity after the packaging date.

The data and values mentioned with respect to WVTR (Water Vapour Transmission Rate) correspond to unsaturated values in accordance with the standard ASTME 398-83, which is generally applied in this field and is known to the person skilled in this art.

DETAILED DESCRIPTION OF THE PREFERRED EMBODIMENTS

Figure 2:
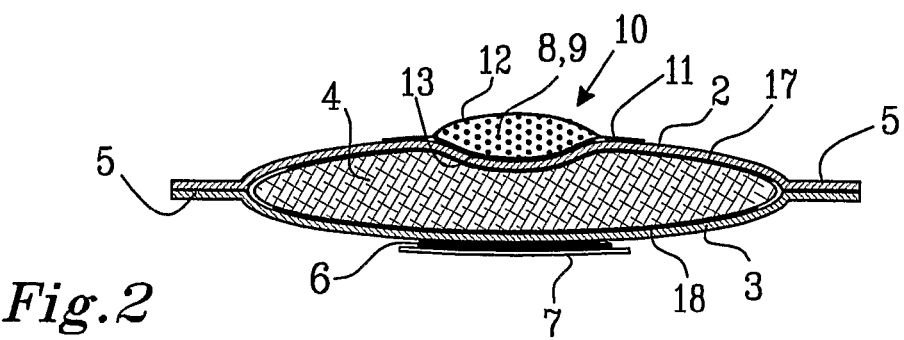
FIG. 2 is a cross sectional view through the absorbent article according to the line II-II in FIG. 1.

FIGS. 1 and 2 show an embodiment of a sanitary napkin 1 which comprises a liquid permeable topsheet 2, a liquid impermeable backsheet 3 and an absorbent structure 4 enclosed there between. The absorbent structure 4 having a first side 17 and a second side 18. The liquid permeable topsheet 2 can be composed of a nonwoven material, e g spunbonded, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The topsheet material may further be composed of tow fibres, which may be bonded to each other in a bonding pattern, as e.g. disclosed in EP-A-1 035 818. Further examples of topsheet materials are porous foams, apertured plastic films etc. The materials suited as topsheet materials should be soft and non-irritating to the skin and be readily penetrated by body fluid, such as urine or menstrual fluid.

The liquid impermeable backsheet 3 may consist of a thin plastic film, e.g. a polyethylene or polypropylene film, a nonwoven material coated with a liquid impervious material, a hydrophobic nonwoven material, which resists liquid penetration. Laminates of plastic films and nonwoven materials may also be used. The backsheet material is preferably breathable so as to allow vapour to escape from the absorbent structure, while still preventing liquids from passing through the backsheet material.

The topsheet 2 and the backsheet 3 have a somewhat greater extension in the plane than the absorbent structure 4 and extend outside the edges thereof to form projecting portions 5. The layers 2 and 3 are connected to each other within the projecting portions 5, e.g. by gluing or welding by heat or ultrasonic. The topsheet and/or the backsheet may further be attached to the absorbent structure by any method known in the art, such as adhesive or welding by heat or ultrasonic etc. The absorbent structure may also be unattached to the topsheet and/or the backsheet.

Fastening means or fasteners in the form of a region 6 of an adhesive is are provided on the side of the backsheet facing away from the wearer during use. The adhesive may releasably attach to the undergarment of the wearer. A release paper 7 protects the adhesive region 6 before use. The adhesive region 6 may have any suitable configuration, such as elongate or transverse strips, dots, full-coated areas etc.

In other embodiments (not illustrated) of absorbent articles other types of fasteners, like friction fasteners, tape tabs or mechanical fasteners like hook-and-loop fasteners etc may be used to fasten the articles to the underwear or around the waist of the wearer. Some absorbent articles are in the form of pants and therefore do not need special fastening means. In other cases the absorbent article is worn in special elastic pants without the need for additional fasteners.

The absorbent structure 4 having a first side 17 and a second side 18 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent structure. It is also common to have absorbent structures comprising layers of different material with different properties with respect to liquid acquisition capacity, liquid distribution capacity and storage capacity. This is well-known to the person skilled in the art and does therefore not have to be described in detail. The thin absorbent bodies, which are common in today's absorbent articles, often comprise a compressed mixed or layered structure of cellulosic fluff pulp and superabsorbent. The size and absorbent capacity of the absorbent structure may be varied to be suited for different uses such as sanitary napkins, pantyliners, adult incontinence pads and diapers, baby diapers, pant diapers, etc.

It is understood that the absorbent article described above and shown in the drawings only represents one non-limiting example and that the present invention is not limited thereto, but can be used in any type of absorbent articles as defined above.

As previously stated an object of the present invention is to provide hygiene products, such as sanitary napkins, pantyliners, diapers, incontinence guards, hygiene tissues etc. suitable for absorbing bodily fluids and simultaneously release a moisture sensitive additive such as for example a probiotic substance that is to be transferred to the skin. The moisture sensitive additive can also be an odour-inhibiting additive, such as zeolites and silica, which is to be exposed, subsequent to the removal of one of the material layers, to the body exudates.

The disclosure pertains to solve the problems associated with providing products comprising moisture sensitive additives, such as problems with deactivation or reduced effect of the additives during storage of the products and costs and effectiveness of manufacturing.

Figure 3:
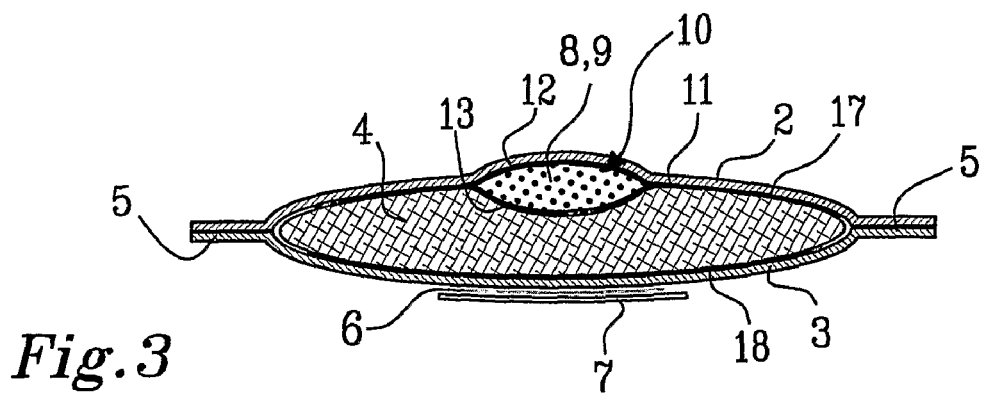
FIG. 3 is a cross sectional view through an alternative embodiment of the absorbent article.

As illustrated in FIG. 1-3, the absorbent article further comprises a water-vapour impermeable carrier member 10 comprising a moisture sensitive additive 8. The carrier member 10 is located on the first side 17 of the absorbent structure 4.

According to FIG. 1-2 the carrier member 10 is located on top of the wearer facing side of the topsheet 2, but may also, as illustrated in FIG. 3, be located between the topsheet 2 and the absorbent structure 4 or, as a less preferred embodiment, between the absorbent structure 4 and the backsheet 3, thus on the second side 18 of the absorbent structure 4.

As illustrated in FIG. 4-7 the carrier member 10 comprises a first 12 and a second 13 water-vapour impermeable material layer, said material layers 12, 13 being sealed together to form a water-vapour impermeable volume 9 there between holding said moisture sensitive additive 8.

As illustrated further in FIG. 4-7, the carrier member 10 can be constructed in different ways.

Figure 4:
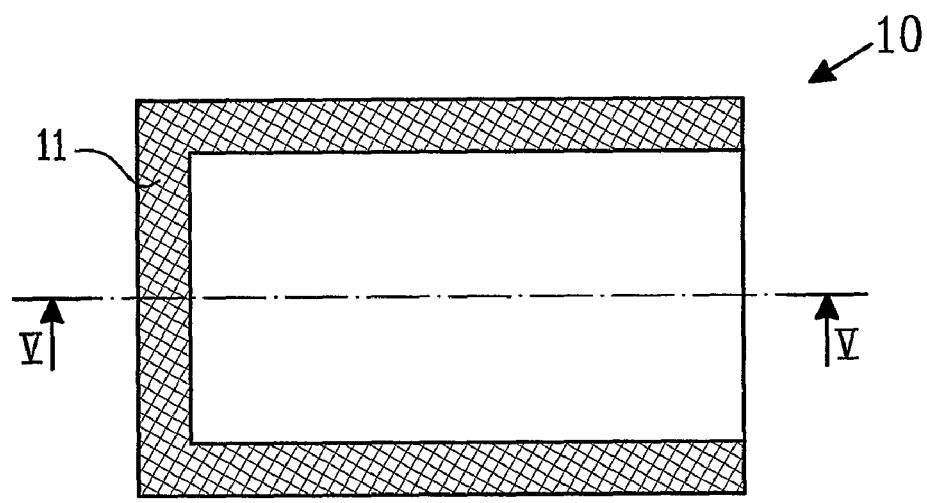
FIG. 4 is a plan view of the carrier member according to the present invention.
Figure 5:
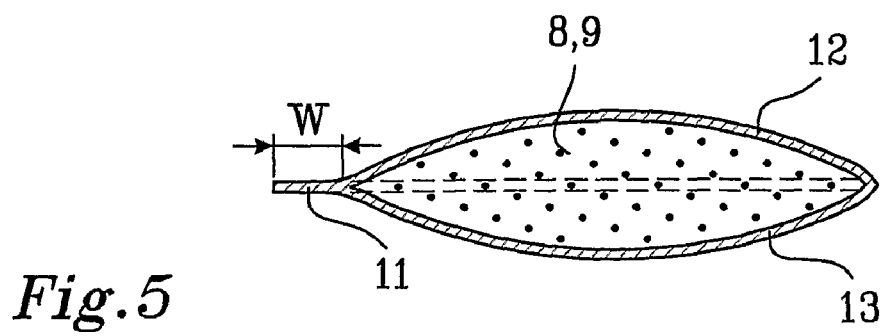
FIG. 5 is a cross sectional view through a carrier member according to the line V-V in FIG. 4.

The carrier member 10 can be formed as shown in FIG. 4-5, by folding one material layer into two material layers 12, 13 and seal together the folded material layer 12, 13 along the open edges.

Figure 6:
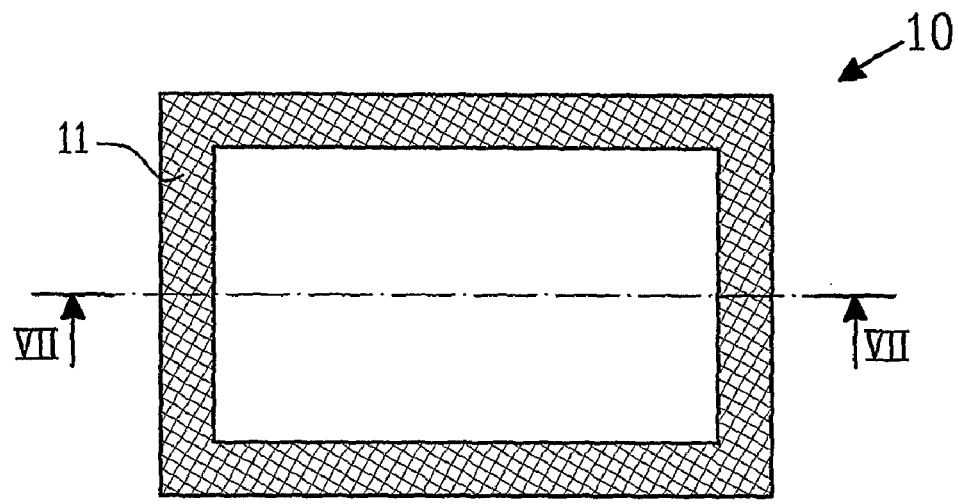
FIG. 6 is a plan view of a carrier member according to an alternative embodiment of the present invention.
Figure 7:
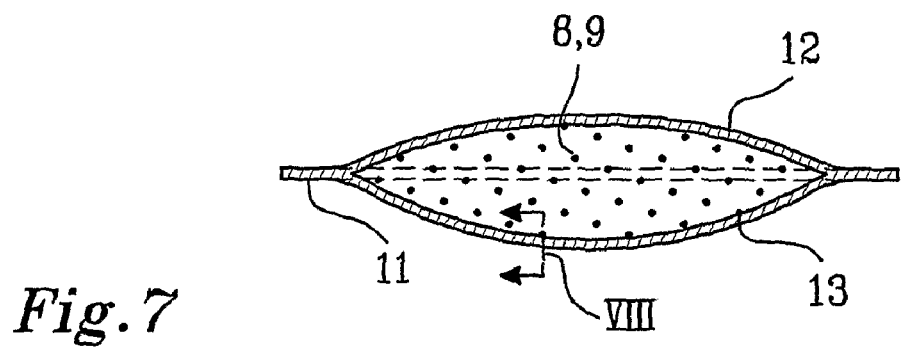
FIG. 7 is a cross sectional view through the carrier member according to the line VII-VII in FIG. 6.

The carrier member can alternatively be formed as shown in FIG. 6-7, by placing two material layers 12, 13 on one another and seal the open edges with respective sealings 11.

The material layers may be produced, at least partially, from one or more polymers suitable for use, the polymers may be chosen from polyethylene, polypropylene, polyesters, polyethylene terephthalate, polyvinylchloride, polyvinyldichloride, cyclic olefinic copolymers, polyolefins, metallized polyolefins, ethylene vinylacetate copolymers, ethylene ethyl acrylate copolymers, ethylene butyl acrylate copolymers, polyamides, polyvinyl alcohol, ionomers, copolymers and mixtures thereof and plastic laminates with ceramic barrier.

Polymeric material with good water vapour barrier properties are polyethylene, polypropylene, polyesters, polyvinyl chloride, polyvinyl dichloride, cyclic olefinic copolymers, metallized polyolefins, plastic laminates with ceramic barriers Aluminium foil, aluminium oxide or silicon oxide or the like is equally suitable water vapour barrier materials for producing said material layer, an example of these latter three materials being Techbarrier S, V, H, T, AT, NR, NY Mitsubishi, Helional WTY (Amcor Flexibles), VA 535670 (metallised PE/PET) (Nordenia), 4364 (Schur-Flexible), Coex HDPE Surlyn (Schur-Flexible), Coex Cheerios (Schur-Flexible). Other materials that may be suitable to use in the laminate in accordance with the invention are waxes, paper, lacquers and adhesives.

Figure 8:
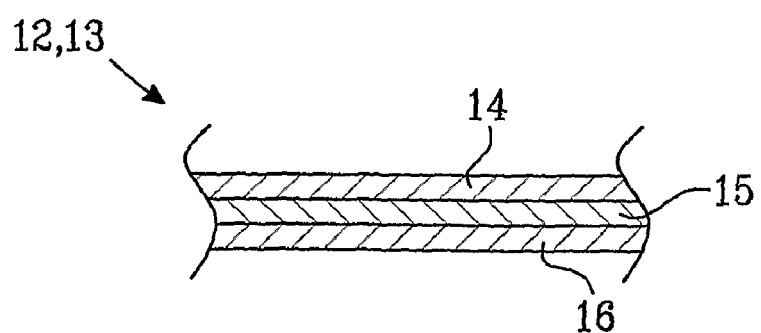
FIG. 8 is a cross sectional view through one embodiment of the first or second material layer of the carrier member according to the present invention.

FIG. 8 illustrates the material layer 12, 13 as a three layer laminate having a protective wear resistant layer 16 intended to lie as an exterior protection layer, a water vapour impermeable intermediate layer 15 and an inner sealing layer 14 intended to face the moisture sensitive additive.

The material layer 12, 13 i.e. the laminate illustrated in FIG. 8 will preferably have a thickness of 10-400 μm, preferably 20-300 μm.

The material intended for forming the water-vapour impermeable material layer 12, 13 is often expensive and preferably the thinnest possible material layer is used while the required strength properties are still maintained. In order to produce a material layer 12, 13 that has good wear strength and can be readily sealed, a less expensive material may be used as outer protective wear resistant layer 16 and/or as inner sealing layer 14. For instance, the material layer 12, 13 may include an inner laminate layer 14 that enables a good seal 11 to be obtained, e.g. polyolefines, ethylene vinylacetat copolymers, ethylene ethyl acrylate copolymers, ethylene butyl acrylate copolymers, polyethylene ethyl acrylate, polyethylene vinyl acetate, polyamides, ionomers or wax, an intermediate laminate layer 15 that consists of a material having good water-vapour impermeablilty to be chosen from the materials aluminium, aluminium oxide, silicon oxide, polyethylene, polypropylene, polyesters, polyvinylchloride, polyvinyldichloride, cyclic olefinic copolymers, polyolefins, metallized polyolefines, polyamide (nylon) or plastic laminates with ceramic barrier and a wear resistant outer layer 16, e.g. polyesters, polyetylene or polypropylene. The material layer 12, 13 may consist of one to ten laminate layers of different materials. Non-limiting examples of laminates are high barrier aluminium laminates and a high barrier aluminium-free laminates, Ceramis®, both from ALCAN Packaging Cramlington Ltd.

Suitable sealing methods are, e.g., ultrasonic welding, heat sealing, heat sealing at low temperatures, or cold sealing. In the case of cold sealing and heat sealing at low temperatures, a sealing layer, such as e.g. polyethylene ethyl acrylate, polyethylene vinyl acetate or wax, is applied to the sealing side of the carrier member. This sealing layer can be applied over the whole of the surface or solely where sealing shall occur, so-called border coating. In order to facilitate heat sealing, the laminate layers used as the water-vapour impermeable material layer and the interior laminate "welding" layer will normally include low density polyethylene (LDPE), optionally co-polymerised with butyl acrylate or vinyl acetate. This enables heat sealing to be effected at high speeds. When sealing said carrier member it is necessary to press the sealing material together around said volume, as in the case for all sealing methods. This is achieved with the aid of cold, hot or slightly heated wheels or sealing jaws and must be effected at a pressure, and temperature and over a given time period that are appropriate for the material chosen and will result in the intended tight sealings and sealing strength.

The material layers may also be glued together to form said sealing.

In order to ensure that the carrier member 10 will prevent the ingress of moisture, it is important that the carrier member 10 is completely closed with tight sealings 11 so that the WVTR of the carrier member 10 will be at most 6 g/m$^2$/24 h measured in accordance with ASTME 398-83 at 37.8° C. (100° F.) and 90% relative humidity, preferably at most 4 g/m$^2$/24 h, and more preferably at most 2 g/m$^2$/24 h, even more preferably at most 1 g/m$^2$/24 h, and even more preferably at most 0.1 g/m$^2$/24 h, even when measured across the sealing 11.

The width W, as measured according to FIG. 5, of the sealing 11 will influence the time it takes for the water-vapour to diffuse into the volume 9. According to one embodiment the sealing has a width W of at least 1 mm, preferably 3 mm and most preferably 5 mm. This will ensure that the moisture sensitive additives 8 will retain their effect for a prolonged time.

It is within the scope of the invention that the absorbent article may comprise two or more of said carrier member containing a moisture sensitive additive, these are preferably located spaced apart in the longitudinal direction of the absorbent article.

In a further (not illustrated) embodiment said carrier member can comprise two or more volumes containing the moisture sensitive additive, these are preferably located spaced apart in the longitudinal direction of the article. In the two above examples it is possible that the two or more carrier members 10 or two or more volumes 9 contain different kinds of moisture sensitive additives. For example one absorbent article 1 contains one carrier member 10 comprising two separate volumes 9, where one of said volumes 9 comprises an odour-inhibitor and the other of said volumes 9 comprises a bacterial composition.

Figure 9A:
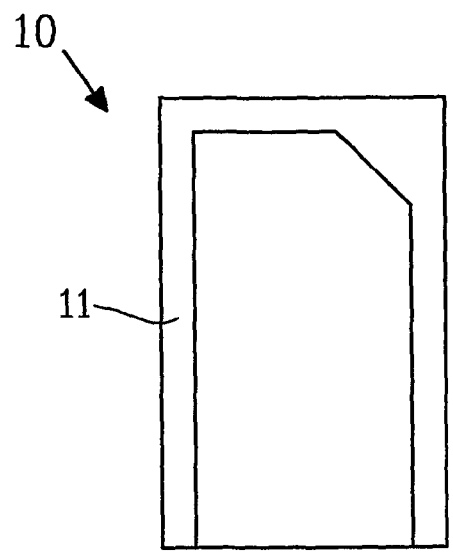
FIG. 9 a-e illustrates carrier members according to embodiments of the invention having different shapes.
Figure 9B:
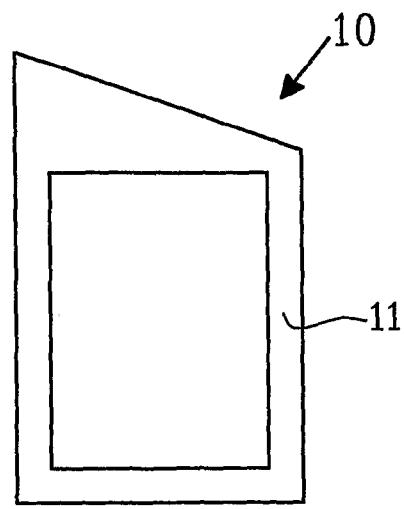
Figure 9C:
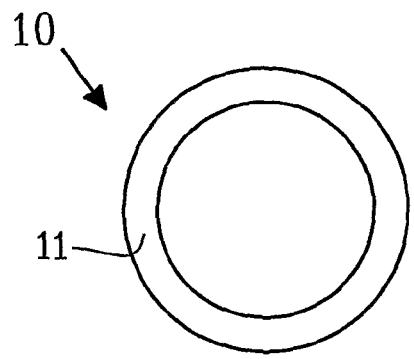
Figure 9D:
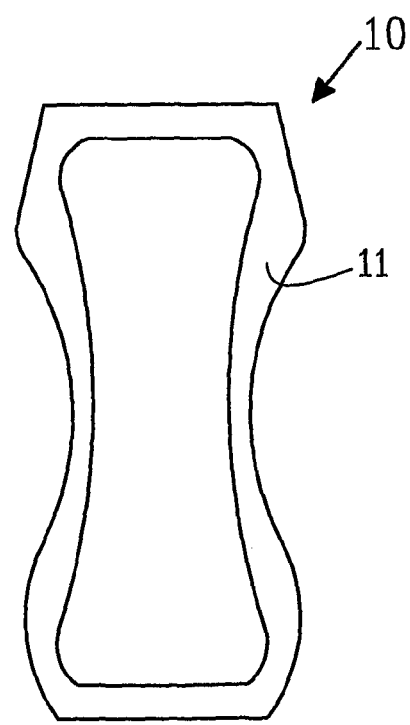
Figure 9E:
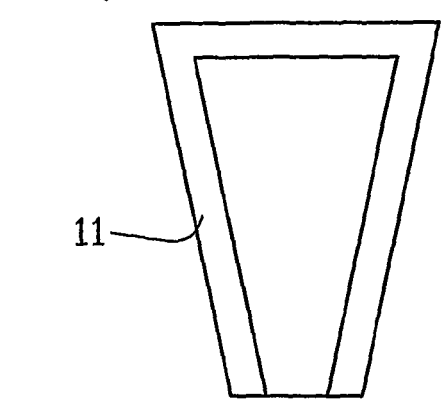

FIG. 9a-e illustrates carrier members having different shapes. FIG. 9a shows a folded elongated carrier member 10 with a chamfered edge allowing a portion near the edge to form a finger grip to enable easy opening and FIG. 9b shows another elongated carrier member 10. FIG. 9c shows a circular carrier member. FIG. 9d shows a sandglass shaped carrier member 10. FIG. 9e shows a folded essentially triangle formed carrier member 10.

According to one aspect the length of said carrier member is 1-15 cm, preferably 2-8 cm, most preferably 2-5 cm. In a further aspect the width of said carrier member is 0.5-5 cm, preferably 0.8-3 cm, most preferably 1-2 cm.

For carrier members 10, as for example according to FIGS. 9c-e, that have a varying width along its length, the scope of the invention should be understood as include all carrier members which at some point along its length exhibit a width as claimed, and equivalents thereof.

Before using the absorbent article 1 one of the material layers 12 or 13 of the carrier member 10 should be removed or ruptured in order to expose the wearer for the bacterial composition or to expose the absorbent article for the odour-inhibiting composition. This may be accomplished in many different ways, for example the carrier member 10 is opened by peeling of one of the material layers 12 or 13 or by squeezing and rupturing one of the material layers 12 or 13. The carrier member may also be opened by a pull string having a free end and while the rest of the pull string is integrated into the carrier member 10. Upon pulling the pull string the material layer/layers 12, 13 will be peeled of or ruptured.

The invention claimed is:

1. An absorbent article comprising:
 an absorbent structure with a wearer facing side and a garment facing side,
 a carrier member, said carrier member comprises first and second water-vapour impermeable material layers, said material layers being sealed together by a sealing to form a water-vapour impermeable volume therebetween, said carrier member being located on the wearer facing side of the absorbent structure, and
 a bacterial composition and delivery vehicle mixture contained in the water-vapour impermeable volume, wherein said bacterial composition is in the form of a dry powder and is dispersed in or applied to the delivery vehicle, wherein said delivery vehicle is a hydrophobic composition that improves protection against moisture from reaching the bacterial composition.

2. The absorbent article according to claim 1, wherein said first or second material layer comprises a metal foil.

3. The absorbent article according to claim 2, wherein said metal foil is aluminum.

4. The absorbent article according to claim 2, wherein said metal foil has a thickness of at least 2 μm.

5. The absorbent article according to claim 2, wherein said metal foil has a thickness of at least 7-10 μm.

6. The absorbent article according to claim 1, wherein said first or second material layer comprises a metal oxide layer or a silicon oxide layer.

7. The absorbent article according to claim 6, wherein said metal oxide layer is an aluminum oxide layer.

8. The absorbent article according to claim 1, wherein said first and second material layers comprise a laminate comprising a polymeric material.

9. The absorbent article according to claim 1, wherein said first or second material layer comprises a polymeric film.

10. The absorbent article according to claim 9, wherein said polymeric film is chosen from polyethylene, polypropylene, polyesters, polyvinyl chloride, polyvinyl dichloride, cyclic olefinic copolymers, copolymers and mixture thereof, metallised polyolefins and plastic laminates with ceramic barrier.

11. The absorbent article according to claim 8, wherein said polymeric material is chosen from polyethylene, polypropylene, polyesters, polyethylene terephthalate, polyvinylchloride, polyvinyldichloride, cyclic olefinic copolymers, polyolefins, metallized polyolefins, ethylene vinylacetate copolymers, ethylene ethyl acrylate copolymers, ethylene butyl acrylate copolymers, polyamides, polyvinyl alcohol, ionomers, copolymers and mixtures thereof and plastic laminates with ceramic barrier.

12. The absorbent article according to claim 8, wherein said laminate comprises at least three laminate layers.

13. The absorbent article according to claim 12, wherein said polymeric material is forming the exterior laminate layer facing away from the bacterial composition.

14. The absorbent article according to claim 1, wherein said first and second material layers comprise a laminate of a metal foil and a polymeric material or a wax.

15. The absorbent article according to claim 14, wherein said laminate comprises at least three laminate layers.

16. The absorbent article according to claim 15, wherein said polymeric material or wax is the interior laminate layer facing the bacterial composition.

17. The absorbent article according to claim 16, wherein said polymeric material is forming the exterior laminate layer facing away from the bacterial composition.

18. The absorbent article according to claim 17, wherein both said interior laminate layer and said exterior laminate layer are formed by a polymeric material or a wax.

19. The absorbent article according to claim 14, wherein said wax is chosen from a plant wax, a mineral wax, an animal wax, a silicon wax and mixtures thereof.

20. The absorbent article according to claim 14, wherein said polymeric material or wax forms said sealing around said water-vapour impermeable volume.

21. The absorbent article according to claim 1, wherein said sealing of said water-vapour impermeable volume has a width of at least 1 mm.

22. The absorbent article according to claim 1, wherein the length of said carrier member is 1-15 cm.

23. The absorbent article according to claim 1, wherein the width of said carrier member is 0.5-5 cm.

24. The absorbent article according to claim 1, wherein the absorbent article comprises a liquid-permeable topsheet and a backsheet, wherein the absorbent structure is located between the topsheet and the backsheet.

25. The absorbent article according to claim 24, wherein said carrier member is located on the wearer facing side of said topsheet.

26. The absorbent article according to claim 24, wherein said carrier member is located between said topsheet and said absorbent structure.

27. The absorbent article according to claim 1, wherein said carrier member is formed by placing two material layers on one another with the bacterial composition there between and sealing the open edges formed between the two material layers.

28. The absorbent article according to claim 1, wherein said one piece of material layer is folded with the bacterial composition located between the folded material layers and the folded material layers are sealed together along the open edges.

29. The absorbent article according to claim 1, wherein said bacterial composition contains lactic acid producing bacteria.

30. The absorbent article according to claim 29, wherein said lactic acid producing bacteria is *Lactobacillus plantarum* 931.

31. The absorbent article according to claim 1, wherein said absorbent article comprises at least two carrier members spaced apart in a longitudinal direction of the absorbent article.

32. The absorbent article according to claim 1, wherein said carrier member upon use of the article is adapted to be opened to release the bacterial composition held therein, by peeling open and/or by rupturing one of the material layers.

33. The absorbent article according to claim 1, wherein said first and second material layers comprise a metal foil.

34. The absorbent article according to claim 1, wherein said first and second material layers comprise a polymeric film.

35. A method of using the absorbent article of claim 1, the method comprising opening the carrier member to release the bacterial composition by peeling open or by rupturing one of the material layers.

36. The absorbent article according to claim 1, wherein the sealing has a width of at least 1 mm.

37. The absorbent article according to claim 1, wherein the sealing has a width of at least 5 mm.

38. A method of forming an absorbent article that includes an absorbent structure, the method comprising:
dispersing a bacterial composition in or applying a bacterial composition to a delivery vehicle,
placing the bacterial composition with the delivery vehicle between two water-vapour impermeable material layers and sealing the material layers together to form a carrier having a water-vapour impermeable volume holding the bacterial composition; and
locating the carrier on a side of the absorbent structure,
wherein said bacterial composition is in the form of a dry powder and said delivery vehicle is a hydrophobic composition that improves protection against moisture from reaching the bacterial composition.

39. The method of forming an absorbent article according to claim 38, comprising sealing the material layers together to form a sealing having a width of at least 1 mm.

* * * * *